(12) United States Patent
Hakim

(10) Patent No.: US 11,650,433 B2
(45) Date of Patent: May 16, 2023

(54) VISUAL LOUPES WITH POINT OF VIEW MODIFICATION

(71) Applicant: Alia Hakim, Lexington, SC (US)

(72) Inventor: Alia Hakim, Lexington, SC (US)

( * ) Notice: Subject to any disclaimer, the term of this patent is extended or adjusted under 35 U.S.C. 154(b) by 0 days.

(21) Appl. No.: 17/567,572

(22) Filed: Jan. 3, 2022

(65) Prior Publication Data

US 2022/0121041 A1    Apr. 21, 2022

Related U.S. Application Data

(63) Continuation of application No. 17/359,289, filed on Jun. 25, 2021, now abandoned, which is a continuation of application No. 17/015,718, filed on Sep. 9, 2020, now Pat. No. 11,061,257.

(51) Int. Cl.
    G02C 7/08       (2006.01)
    G02B 27/01      (2006.01)
    G02C 7/14       (2006.01)
    G02B 25/00      (2006.01)

(52) U.S. Cl.
    CPC .......... *G02C 7/088* (2013.01); *G02B 27/0172* (2013.01); *G02C 7/14* (2013.01); *G02B 25/007* (2013.01)

(58) Field of Classification Search
    CPC ............ G02B 23/02; G02B 2027/0178; G02B 27/0172; G02B 27/017; G02B 2027/0132; G02B 5/04; G02B 25/001; G02B 23/16; G02B 27/0955; G02B 5/08; G02B 7/1805; G02B 17/06; G02B 6/0018; G02B 6/4214; G02B 23/145; G02B 23/04; G02B 25/00
    See application file for complete search history.

(56) References Cited

U.S. PATENT DOCUMENTS

| 2,123,682 A | 7/1936 | Wingate |
| D161,885 S  | 2/1951 | Warner  |
| 2,618,199 A | 11/1952 | Evans  |

(Continued)

FOREIGN PATENT DOCUMENTS

| JP | 5016256 | 9/2012 |
| WO | WO 2013177004 | 11/2013 |

(Continued)

OTHER PUBLICATIONS

Chang, "Demistifying Custom Loupes," SurgiTel, 2002, 5 pages.

(Continued)

*Primary Examiner* — Mustak Choudhury
(74) *Attorney, Agent, or Firm* — Fish & Richardson P.C.

(57) ABSTRACT

A device can include glasses including one or more lenses that permit a wearer a broad view of the environment from a first perspective and contact members having one or more contact-surfaces formed to secure the glasses to a head of the wearer while the wearer is wearing the device. The device can include one or more loupes, each loupe including a redirection member structured to redirect image light that is received by the loupe; one or more magnifying members structured to magnify the image light; a viewport structured to allow passage of the magnified image light. The loupe is secured through one of the lenses such that the magnified image light is presented though the viewport to an eye of the wearer while the wearer is wearing the device.

18 Claims, 14 Drawing Sheets

(56) References Cited

U.S. PATENT DOCUMENTS

| | | | |
|---|---|---|---|
| 4,077,703 | A | 3/1978 | Pablo |
| 6,120,145 | A | 9/2000 | Lyst et al. |
| 6,280,031 | B1 | 8/2001 | Zerkle |
| 6,830,331 | B2 | 12/2004 | Jojiki et al. |
| 7,242,522 | B2 | 7/2007 | Kanai |
| 7,283,300 | B2 | 10/2007 | Jojiki |
| 7,322,697 | B2 | 1/2008 | Jojiki |
| 7,494,219 | B2 | 2/2009 | Shahkarami |
| 8,917,459 | B2 | 12/2014 | Klein et al. |
| 2003/0169494 | A1* | 9/2003 | Porter .................. G02B 27/025 351/158 |
| 2006/0133254 | A1* | 6/2006 | Toshiaki .............. G01C 15/002 369/100 |
| 2010/0305436 | A1* | 12/2010 | Chen .................... A61B 5/0059 600/431 |
| 2016/0334644 | A1* | 11/2016 | Garafolo ................. G02C 9/02 |
| 2017/0052391 | A1* | 2/2017 | Fass ..................... G02B 17/045 |
| 2018/0136489 | A1* | 5/2018 | Hellström ............ G02B 25/004 |
| 2020/0117025 | A1 | 4/2020 | Sauer et al. |

FOREIGN PATENT DOCUMENTS

| | | |
|---|---|---|
| WO | WO 2016182488 | 11/2016 |
| WO | WO 2017147235 | 8/2017 |

OTHER PUBLICATIONS

Lumadent.com [online], "Ergoprism", published on or before Sep. 9, 2020, [retrieved on Dec. 1, 2020], retrieved from URL<https://lumadent.com/ergoprism>, 5 pages.

PCT International Search Report and Written Opinion in International Appln. No. PCT/US2021/049703, dated Dec. 22, 2021, 14 pages.

Smallwood, "What are the Benefits of Using Surgical/Dental Loupes?" L.A. Lens Blog, retrieved from URL <https://www.la-lens.com/blogs/in-the-news/16317588-what-are-the-benefits-of-using-surgical-dental-loupes?_pos=1&_SID=20541bfe4&_ss=r>, Dec. 15, 2014, 5 pages.

Valachi, "Neck health: the three ergonomic criteria for loupes selection, Dental Economics, retrieved from URL <https://www.dentaleconomics.com/dental-office-design/equipment-and-furniture/article/16387185/neck-health-the-three-ergonomic-criteria-for-loupes-selection," Sep. 1, 2018, 12 pages.

Bryant.dental [online], "Bryant Dental: Dental Loupes of the Future," available on or before Aug. 27, 2018, via Internet Archive: Wayback Machine URL <http://web.archive.org/web/20180827220654/https:/bryant.dental/>, retrieved on Aug. 12, 2022, URL<https:/bryant.dental/>, 3 pages.

Mooptics.com [online],"Vinkep loupes," available on or before Aug. 9, 2020, via Internet Archive: Wayback Machine URL <https://web.archive.org/web/20200809171010/https://mooptics.com/vinkep-loupes/> retrieved on Aug. 11, 2022, URL<https://mooptics.com/vinkep-loupes/>, 8 pages.

Pentaxloupes.com [online], "Pentax Loupes," available on Dec. 2, 2020, and believed to be available before Sep. 8, 2020, via Internet Archive: Wayback Machine URL <http://web.archive.org/web/20201202122702/https:/www.pentaxloupes.com/>, retrieved on Aug. 12, 2022, URL <https://www.pentaxloupes.com/#features>, 12 pages.

\* cited by examiner

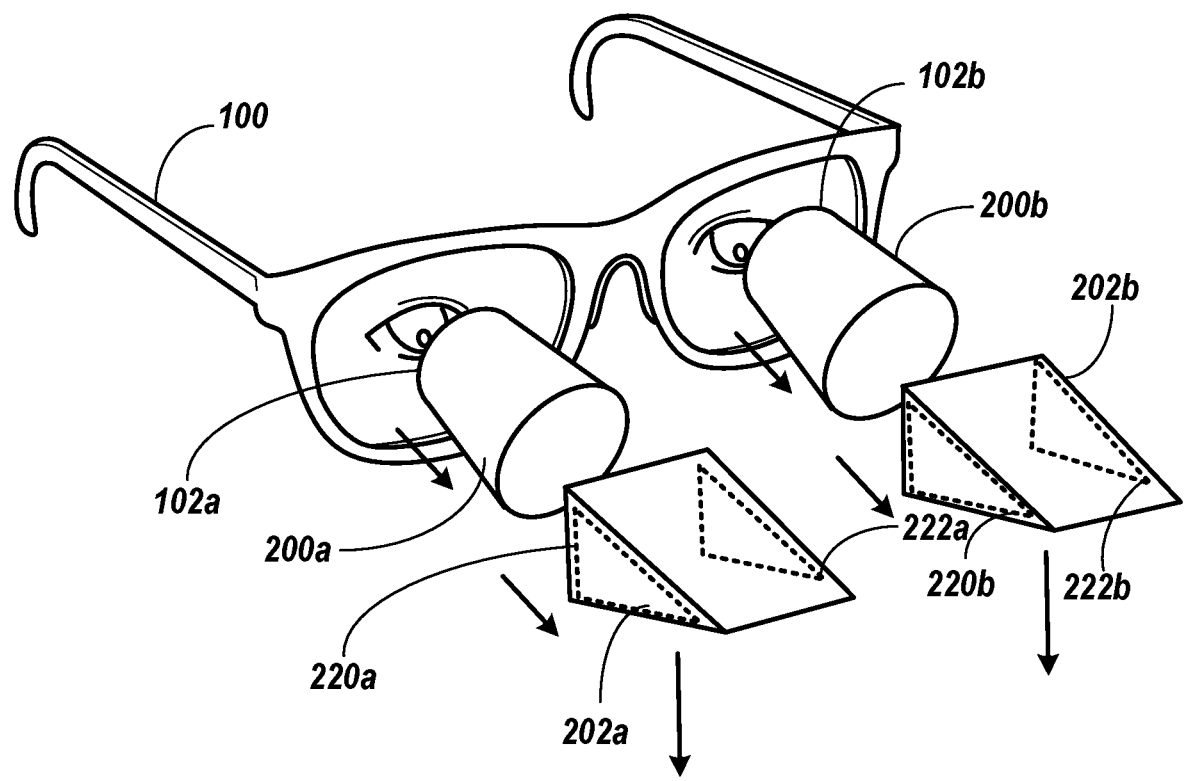
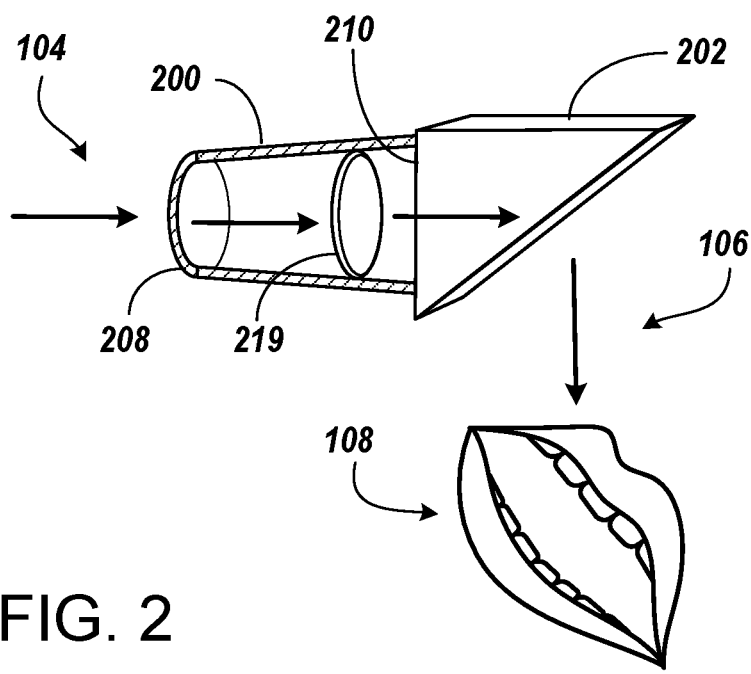
FIG. 2

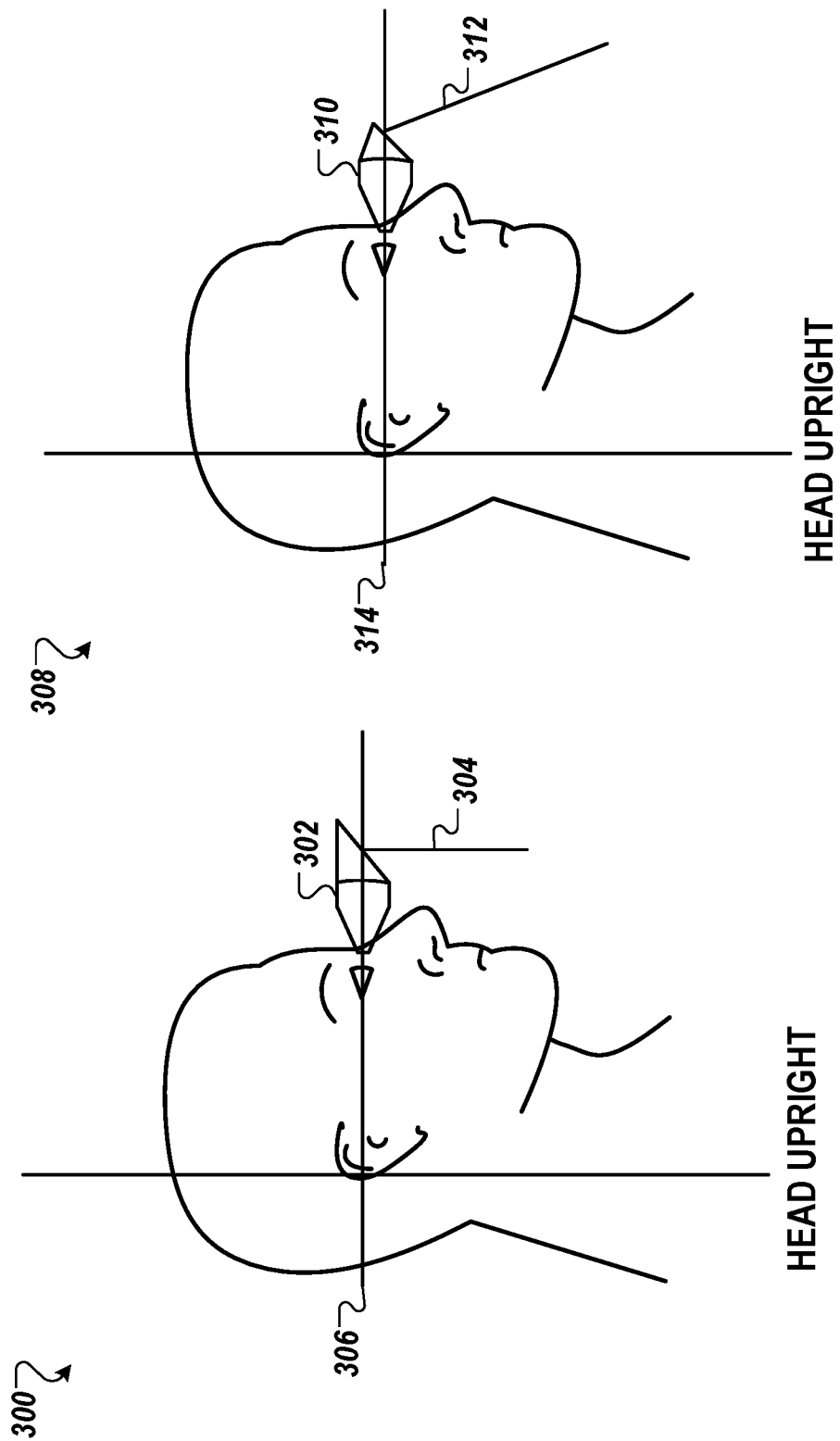

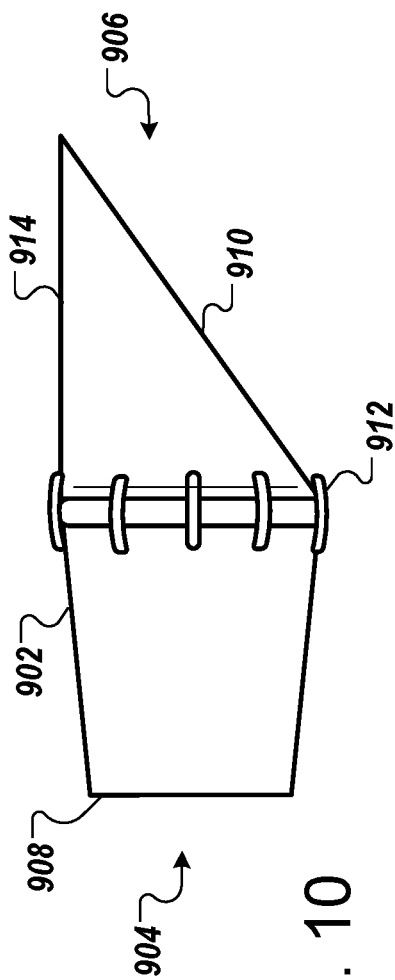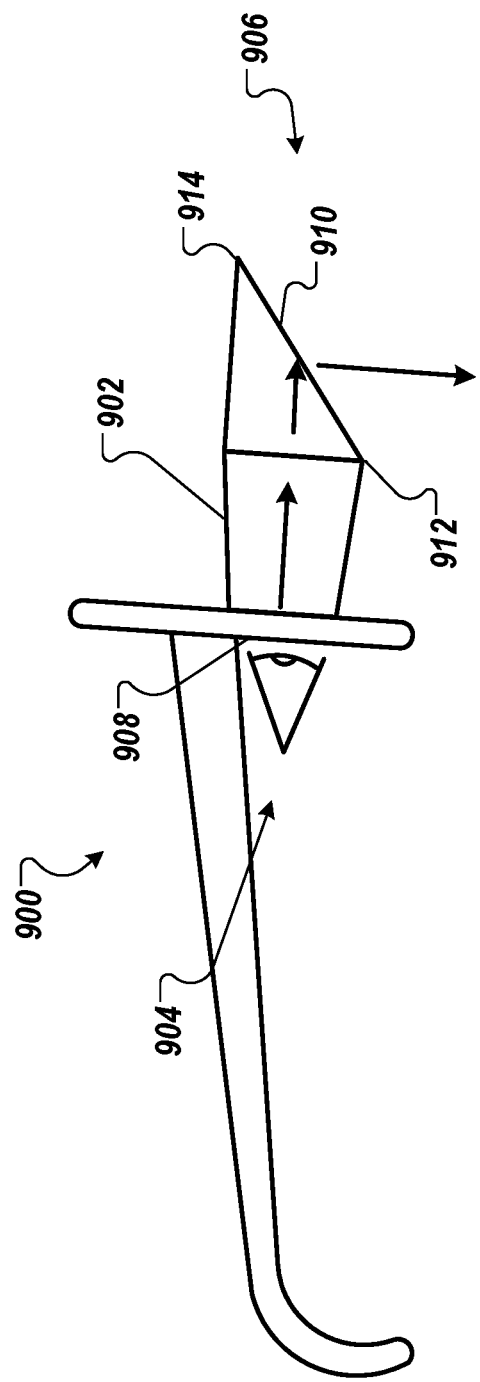

VISUAL LOUPES WITH POINT OF VIEW MODIFICATION

TECHNICAL FIELD

This application is a continuation of U.S. patent application Ser. No. 17/359,289, filed Jun. 25, 2021, which is a continuation of U.S. patent application Ser. No. 17/015,718, filed on Sep. 9, 2020, both of which are incorporated herein by reference in their entirety.

TECHNICAL FIELD

This document describes visual loupes.

BACKGROUND

A loupe is a magnification device used to permit a wearer to see small details more closely and at an increased size. Unlike a magnifying glass, a loupe often does not have an attached handle, and its focusing lens(es) can be contained in an opaque cylinder or cone or fold into an enclosing housing that protects its lenses when not in use. Loupes are sometimes also called hand lenses.

SUMMARY

An optical medical device can be used to provide an ergonomic head-position. The device can include glasses including one or more lenses that permit a wearer a broad view of the environment from a first perspective and contact members having one or more contact-surfaces formed to secure the glasses to a head of the wearer while the wearer is wearing the device. The device can include one or more loupes, each loupe including a redirection member structured to redirect image light that is received by the loupe; one or more magnifying members structured to magnify the image light; a viewport structured to allow passage of the magnified image light. The loupe is secured through one of the lenses such that the magnified image light is presented though the viewport to an eye of the wearer while the wearer is wearing the device. The presented magnified image light provides the wearer with a magnified view of the environment from a second perspective as a result of the structure of the loupe.

A coupleable optical device includes a coupling fixture; an ingress port; an egress port; and a redirection member structured to redirect light. The ingress port is positioned to deliver ingress light to the redirection member. The egress port is positioned to delivery egress light to a loupe while the coupling fixture couples the coupleable optical device to the loupe. The ingress light is angularly offset from the egress light such that a view axis of the loupe is angularly offset from the ingress light while the optical device is coupled to the loupe.

Implementations can include some, all, or none of the following features. Each redirection member comprises at least one optical prism. Each redirection member comprises at least one mirror. Each loupe further comprises an integral housing that fixedly secures the redirection member, the magnification member, and the viewport of the loupe. The integral housing comprises a least one of the group consisting of i) a multi-part clamshell with snap-fasteners ii) metal structures secured with removable fasteners, and iii) a plastic member secured to another element of the optical device with an adhesive. Each loupe comprises a proximal end near the wearer when the wearer wears the optical device; and a distal end away from the wearer when the wearer wears the optical device; and the integral housing fixedly secures: the viewport at the proximal end; the magnification member between the proximal end and the distal end; and the redirection member at the distal end. Each loupe further comprises: an integral housing that fixedly secures the magnification member, and the viewport of the loupe; and a coupleable housing distinct from the integral housing, the coupleable housing fixedly securing the redirection member. The coupleable housing of each loupe is removably coupled to the integral housing of the loupe. The coupleable housing of each loupe is removably coupled to a particular element of the optical device. The particular element of the optical device is a receiving fixture of the loupe, the receiving fixture being distinct from the integral housing. The particular element of the optical device is the glasses. The couple housing comprises a coupling fixture selected from the list consisting of i) a friction fitting, ii) a snap fitting, iii) a threaded screw, iv) an adhesive, and v) a weld. The second perspective is offset from the first perspective by an offset angle that is at least 90°. The second perspective is offset from the first perspective by an offset angle that is one of the group consisting of 70°, 60°, 45°, and 90°. The second perspective is substantially perpendicular to the first perspective. The loupe presents to the wearer a magnified view of the environment from a second perspective as a result of the structure of the redirection member in that the second perspective is parallel to an egress surface of a prism of the redirection member. The glasses are personal protection equipment (ppe) that include two lenses configured and directed to permit a wearer a broad view of an environment from a first perspective and two loupes.

Implementations can provide some, all, or none of the following advantages. A device can be provided to a wearer of the device that allows for a more ergonomic body-posture while also providing a magnified view of an environment, such as a work area. For example, in order to alleviate a possible need to tilt the head down to see the work area surrounding the wearer's hands, a device can provide the wearer with a different angle than his or her unaided angle of view. This can allow the wearer to work with his or her hands for extended periods of time, day after day, with reduced neck and eyestrain. For example, clinicians such as dental professionals often work in an environment in which they must look down onto a patient and into the patient's mouth. This technology can provide the desired view of the environment without the need for a wearer to tilt his or her head in a way that can cause repetitive use injury.

DESCRIPTION OF DRAWINGS

FIG. 2 shows a point of view that has been modified with an optical medical device.

FIGS. 3A and 3B show head angles and view angles.

FIG. 10 shows a side view of the coupleable-housed device.

FIG. 11 shows a side view of the coupleable-housed device.

DETAILED DESCRIPTION

When performing medical procedures such as dental cleaning, a clinician is often required to look down at a patient or work area. This document describes optical medical devices that allow the clinician to achieve this downward view while maintaining a neutral head-angle. Visual loupes can incorporate elements to redirect light. For example, a prism may be housed in a housing that is integral to, or coupled to, magnifying loupes in order to receive an image from below the loupes. These loupes may be integrated into personal protective equipment (PPE) such as protective glasses.

While performing these procedures, clinicians may otherwise need to tilt their head and/or cast their gaze down, which may cause fatigue to the clinician and in some cases cause the clinician to develop repetitive-stress type injuries. Use of devices described in this document can allow the clinician to perform the same procedure with a more ergonomic head-angle, which can reduce or alleviate the need to tilt the head or cast a gaze downward. This can advantageously allow a clinician to perform procedures with greater comfort, with lower risk of injury, and at greater lengths of time if momentary breaks to stretch or relieve are not needed.

Figure 1:
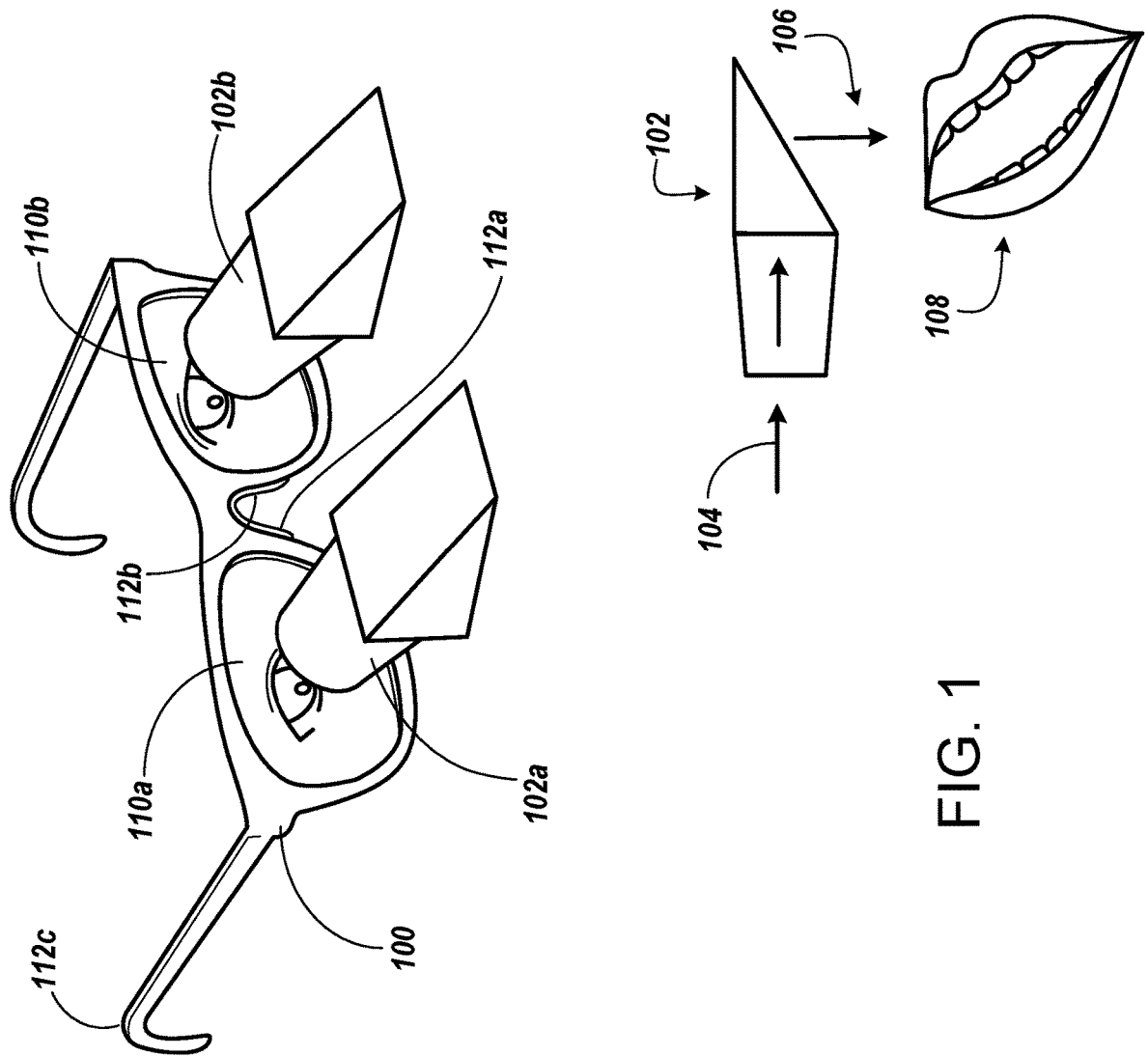
FIG. 1 shows an optical medical device for providing an ergonomic head-position.

FIG. 1 shows an optical medical device 100 for providing an ergonomic head-position. In this example, the device 100 is a set of protective glasses that have loupes 102a and 102b incorporated into lenses of the glasses. These loupes 102 can allow the wearer to have a horizontal view 104 that is magnified and bent to a vertical (or nearly vertical) view 106 oriented to a patient 108 or work area.

The device 100 can include one or more lenses 110a and 110b permitting the wearer a broad view of the environment from a first perspective. In this example, the lenses 110 take the form of a pair of lenses in PPE glasses, though other configurations are possible. For example, a single lens can for be used a face shield, or a single lens can be used in a pair of glasses. The lens may be constructed from a generally clear or tinted material such as a polymer or glass material.

The device 100 can include contact members 112 having one or more contact-surfaces formed to secure the glasses to a head of the wearer while the wearer is wearing the device. In this example, the device 100 includes nose-pads 112a and 112b to contact the wearer's nose and also stems 112c and 112d to contact the wearer's head and ears. Other configurations can include a strap or band that contacts the wearer's head.

The loupes 102 are secured through the lenses 110 such that magnified image light is presented though the viewport to an eye of the wearer while the wearer is wearing the optical device. By being positioned the loupes 102 in the lenses 110, the wearer is able to view through the viewport by orientating the wearer's eyes to the viewports, or may view the environment through the lenses 110 by orienting the wearer's eyes away from the viewport.

This magnified image light provides the wearer with a magnified view of the environment from a second perspective as a result of the structure of the loupe. For example, a magnifying member can magnify the image light, causing objects to appear larger than otherwise, given their size and distance from the wearer's eye. A redirection member can redirect light so that the view presented by the image light is different than the point of view the wearer has when viewing the environment through the lenses only.

FIG. 2 shows a point of view that has been modified with an optical medical device 100. Each loupe 102 includes two substructures, a magnifying member 200 and a redirection member 202. Generally speaking, the magnifying member 200 provides the wearer with magnification, and the redirection member 202 provides the wearer with an altered point of view. As such, the wearer can work with his or her hands around his or her waist or chest level (e.g., perform a clinical procedure on a patient, work with a mechanical device) and to observe this work while keeping his or her head at a neutral angle.

The redirection members 202 are structured to redirect image light that is received by the loupe 102. In some examples, one or more optical prisms of the redirection member 202 can refract light, changing the angle of travel of light through the loupe 102. In some examples, one or more mirrors of the redirection member 202 can reflect light, changing the angle of travel of light through the loupe 102. Some examples may use other structures to redirect the light, and combinations of different types of structures may be used.

The magnifying members 200 are structured to magnify image light. That is, images carried by light that passes through the loupe 102 may be magnified in the view of the wearer. To create this magnification effect, one or more optical lenses may be positioned in the magnification members 200.

Each loupe 102 can include a viewport 208 to allow passage of the magnified image light. In some cases, the viewport 208 may include a circular aperture with a lens or transparent obstructing member that is shaped to seal the loupe 102 from the environment. Such a seal can prevent the ingress of environmental debris, while allowing the object light to be transmitted to the wearer's eye.

The structure of the loupe 102 can operate to present to the wearer a magnified view of the environment from a second perspective 106 that is different than the wearer's natural perspective 104 as a result of the structure of the redirection member 202. For example, a prism of the redirection member 202 may include an egress surface 210 from which the light image egresses the redirection member 202. This egress surface may be perpendicular (i.e., normal) to the wearer's perspective 104 and parallel to the modified perspective 106. Then, the light image can pass through one or more lenses 210 of the magnification member 200 to be magnified. Shown also are third surfaces 220a and 220b, and fourth surfaces 222a and 222b, of the prisms of the redirection members 202a and 202b.

Figure 3B:
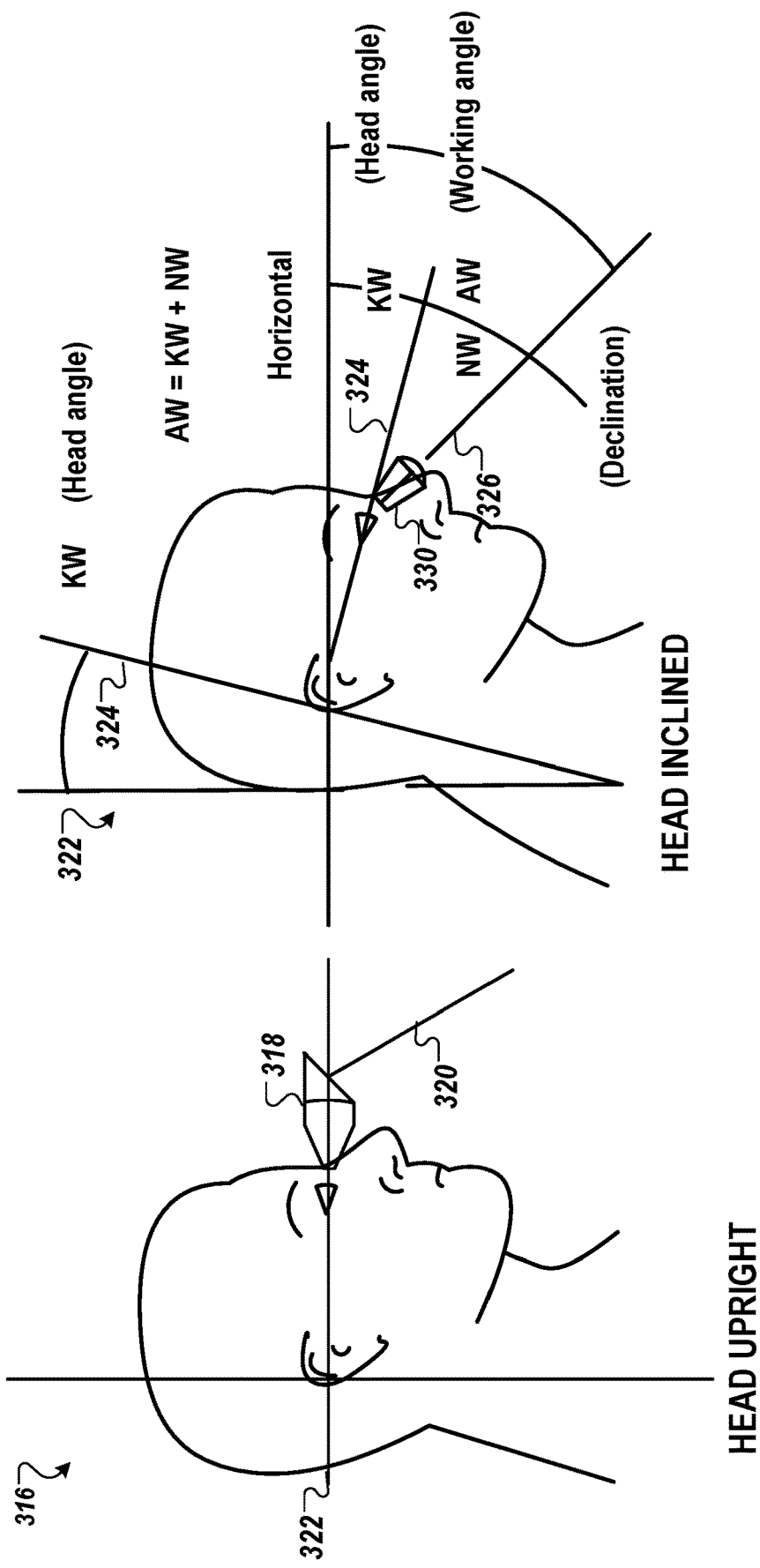

FIGS. 3A and 3B show head angles and view angles.

A wearer 300 is shown wearing an optical medical device 302 that is configured to redirect the wearer's view by an angle 304 of 90°. This can allow the wearer 300 to work with his or her hands near his or her body and view his or her work while holding his or her head angle 306 at parallel to the horizon. This configuration may be useful, for example, for a clinician performing a procedure on a patient or a craft-maker leaning back in their chair and holding a scale-model and paintbrush near his or her body.

In some cases, the angle 304 may be substantially perpendicular to the wearer's view angle, but not precisely 90°. For example, the angle 304 may be between 85° and 95°. Using an angle that is substantially perpendicular can allow for personal modifications based on a particular wearer's physiology. Some wearer's may have a natural head-angle that is not exactly horizontal, may have a natural gaze angle that is not exactly horizontal, or may have arm, shoulder, or neck physiology that makes them feel more comfortable working slightly forward of where the truly and strictly perpendicular angle 304 would be.

A wearer 308 is shown wearing an optical medical device 310 that is configured to redirect the wearer's view by an angle 312 of 70°. This can allow the wearer 308 to work with their hands lowered and extended from their body and view their work while holding their head angle 314 at parallel to the horizon. This configuration may be useful, for example, for a seated electronics assembler soldering components on a table or a jeweler grinding a stone on a grinding wheel.

A wearer 316 is shown wearing an optical medical device 618 that is configured to redirect the wearer's view by an angle 320 of 60°. This can allow the wearer 308 to work with his or her hands extended from his or her body and view his or her work while holding his or her head angle 314 at parallel to the horizon. This configuration may be useful, for example, for a wood-worker or metal-worker doing fine-detail work that wishes to keep his or her face away from cutting surfaces of a machine. Other angles, such as 45°, may be used.

A wearer 322 is shown wearing loupes 330 that do not have a redirection member coupled to the loups 330. As such, to view work near his or her hands, the wearer 322 tilts his or her head at an angle 324 and casts his or her gaze at an angle 326.

Figure 4:
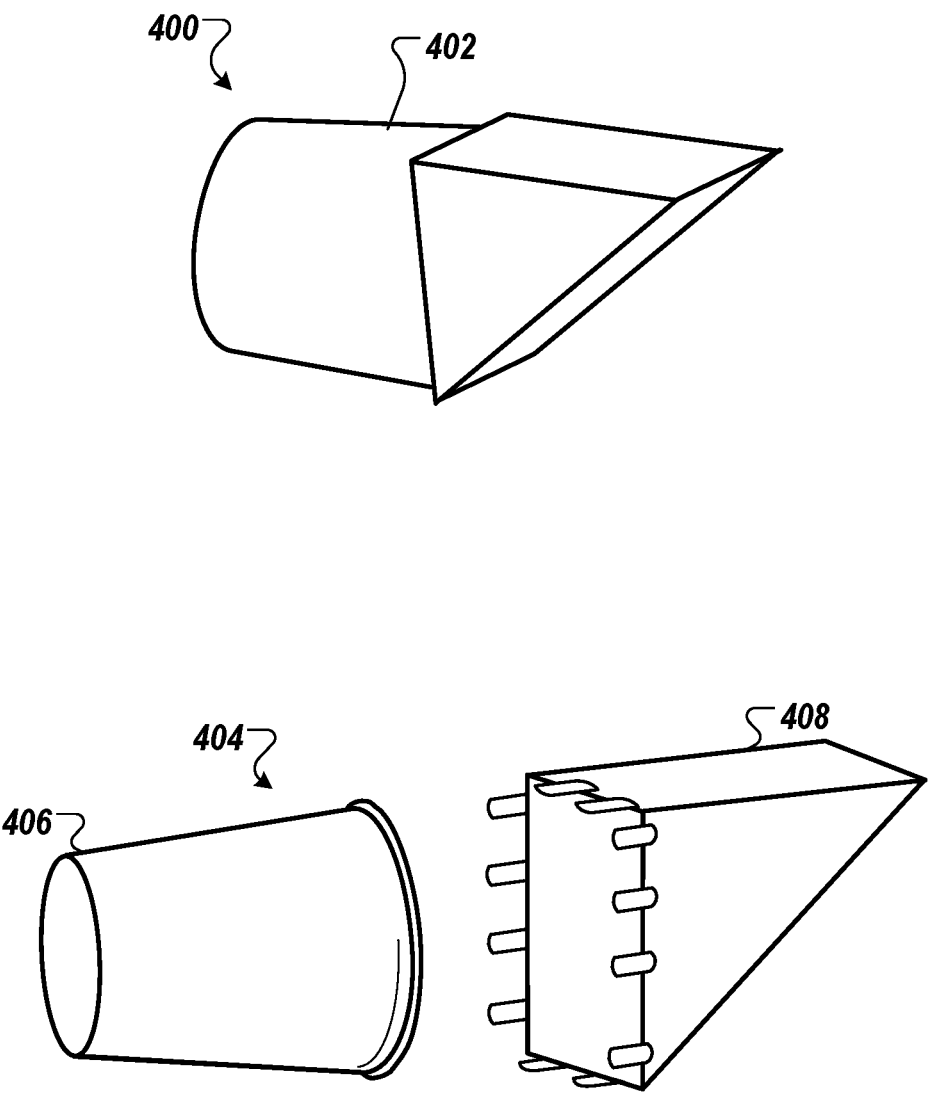
FIG. 4 shows side views of optical medical devices.

FIG. 4 shows side views of optical medical devices 400 and 404.

The device 400 has a single integral housing 402. This integral housing 402, once assembled, forms a single housing that is designed to house both a redirection member (not shown) and a magnification member (not shown) within the housing. As will be appreciated, the integral housing may be assembled from more than one piece, and may be disassembled (e.g., for maintenance), but is generally structured to remain as a single piece in use. As such, the device 400 may be sold as a single unit, either on its own, or as a component of PPE (e.g., glasses sold with two such devices 400).

The device 404 has a magnification member 406 and a redirection member 408 that are removably coupleable together. This coupling may be accomplished by the wearer of the device 404. As such, the components 406 and 408 of the device 404 may be sold separately. For example, a customer may purchase PPE with two magnification members 406. The wearer may also separately purchase two redirection members 408 and may couple the redirection members 408 onto the magnification members 406.

Figure 5:
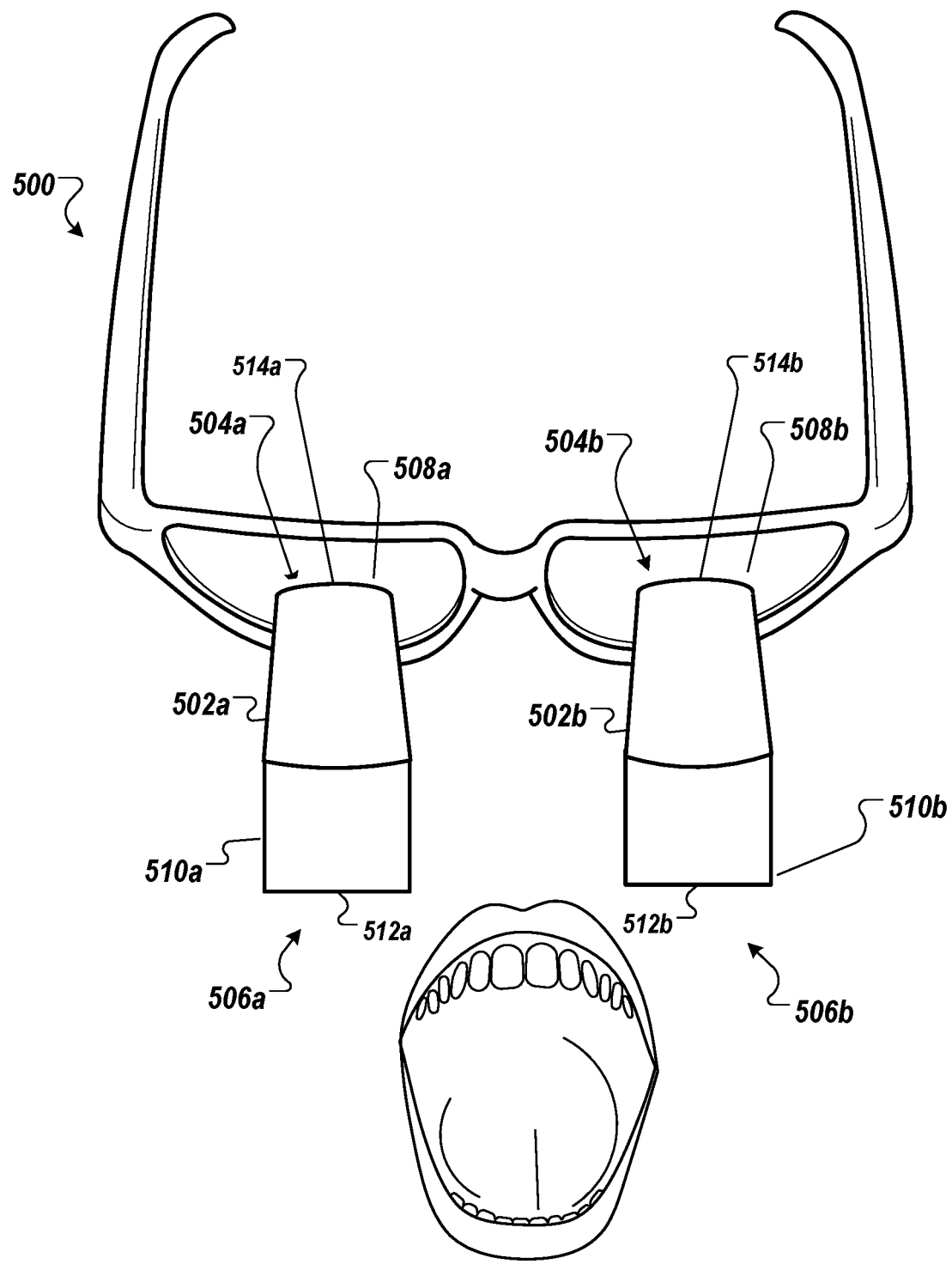
FIG. 5 shows a top view of an integrally-housed device.
Figure 6:
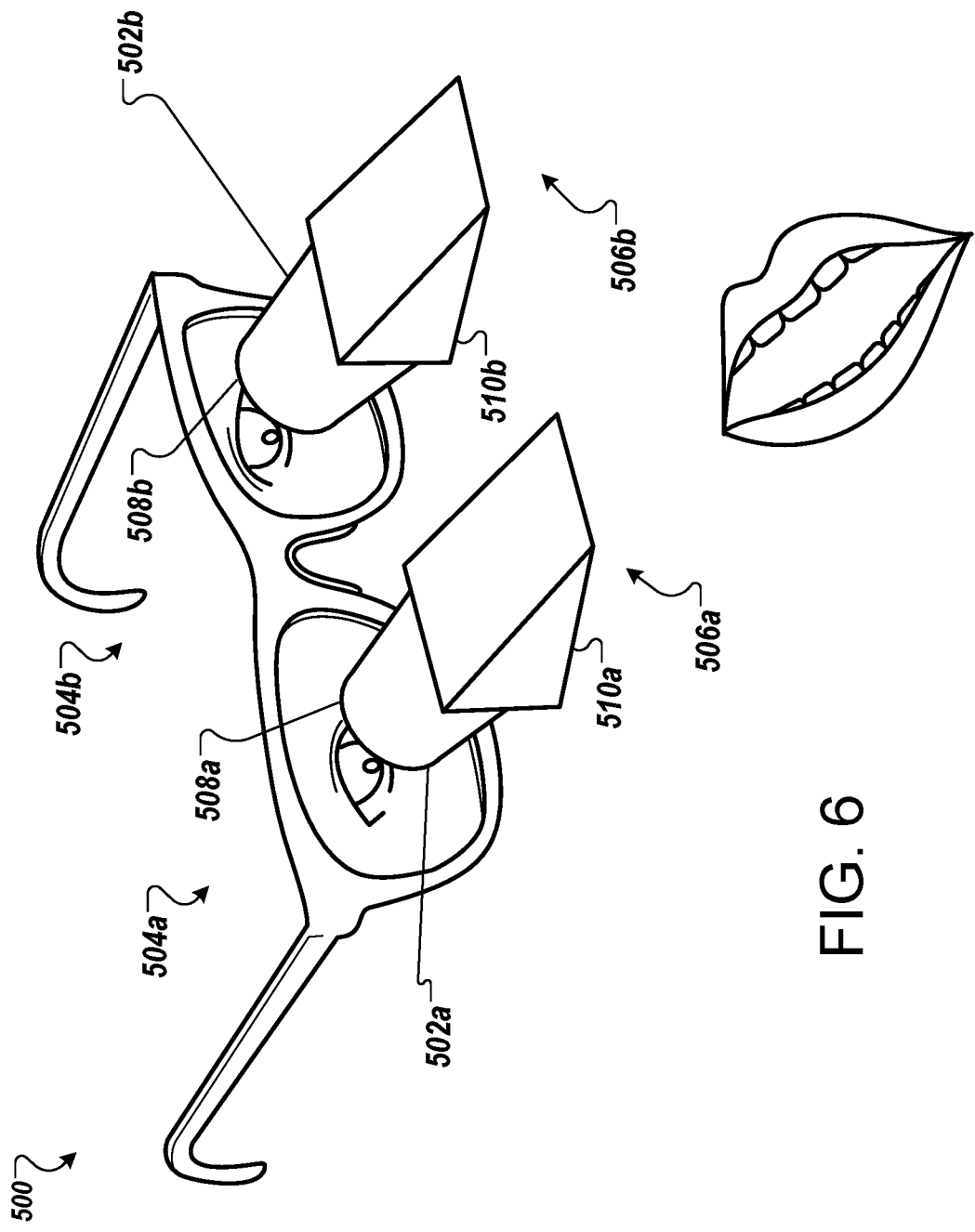
FIG. 6 shows a perspective view of an integrally-housed device.
Figure 7A:
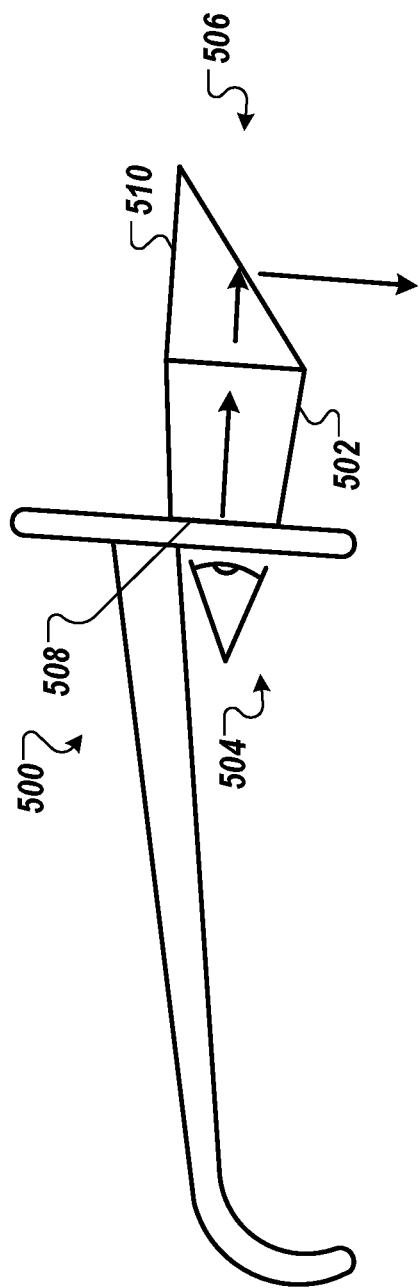
FIGS. 7A and 7B show side views of an integrally-housed device.
Figure 7B:
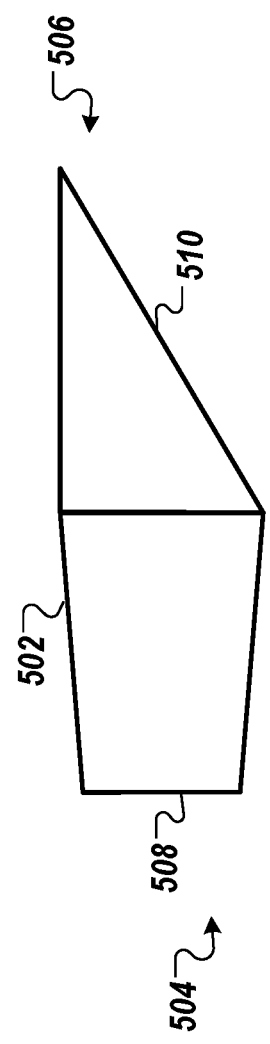
Figure 8:
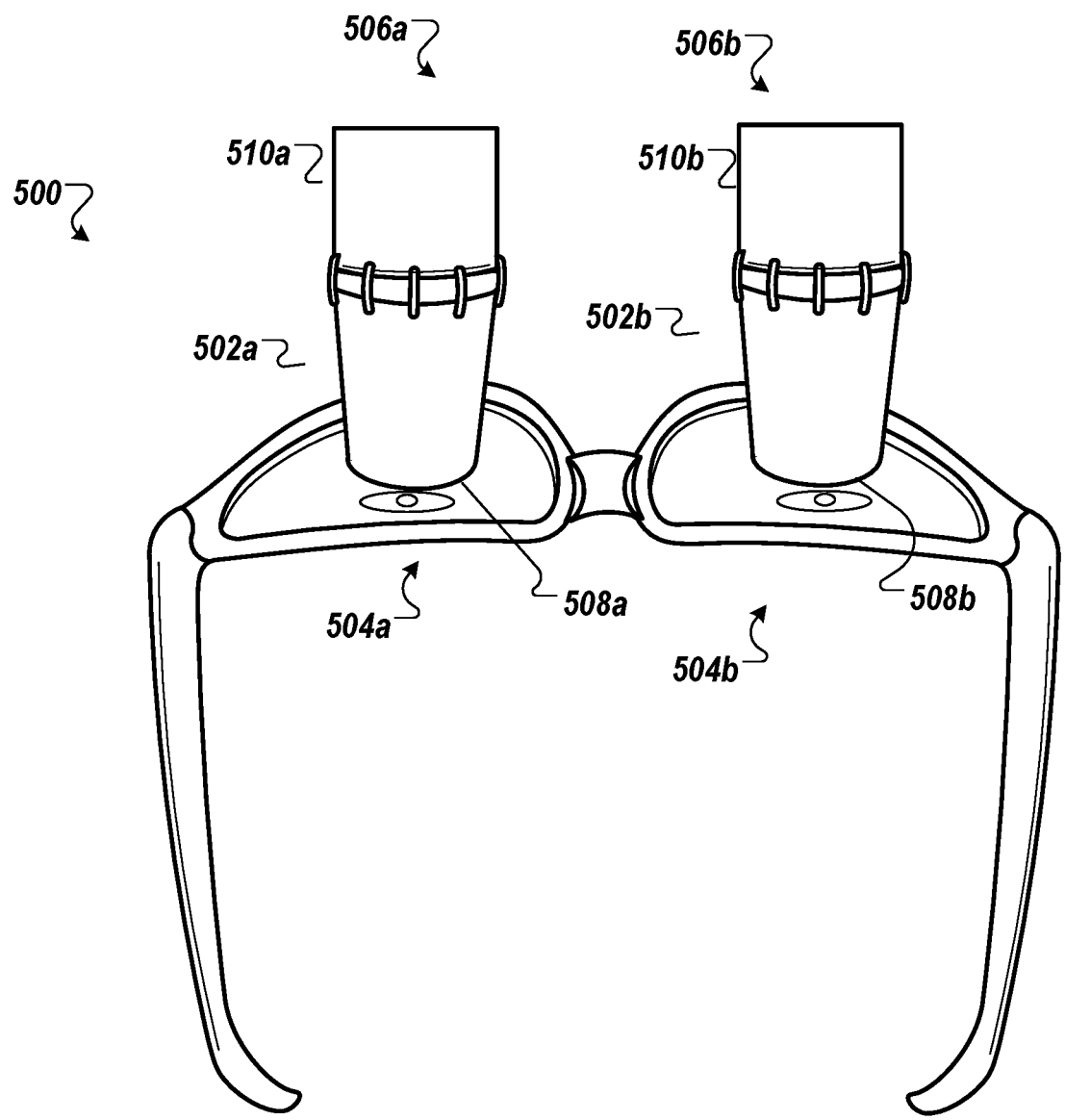
FIG. 8 shows a bottom view of an integrally-housed device.

FIG. 5 shows a top view of an integrally-housed device 500. FIG. 6 shows a perspective view of the integrally-housed device 500. FIGS. 7A and 7B show side views of the integrally-housed device 500. FIG. 8 shows a bottom view of an integrally-housed device 500.

Device 500 includes two loupes 502 that each has an integral housing that fixedly secures a redirection member 510, a magnification member, and a viewport 508 of the loupe. This integral housing can take include one or more features to secure these elements.

In some implementations, the integral housing includes a multi-part clamshell with snap-fasteners. For example, two or more portions of the housing may be manufactured via an injection-molding process with indexing surfaces to hold the magnification member and the redirection member within the housing. In assembly, this clamshell can be snapped together to form the integral housing of the loupe 502.

In some implementations, the integral housing includes metal structures secured with removable fasteners. For example, through-holes in the integral housing may allow for fastening with bolts secured with either nuts or threads tapped into the holes. In another example, pins or roll-pins may be used to secure the integral housing.

In some implementations, the integral housing includes a plastic member secured to another element of the optical device with an adhesive. For example, a clamshell of the integral housing may be adhered to a retaining member of the redirection member and to the protective lenses with an adhesive such as an epoxy or cyanoacrylate.

The distal end 506 includes an ingress port 512 positioned to deliver ingress light to the redirection member 510. For example, the ingress port 512 may include a surface of a prism of the redirection member 510. The proximal end 504 includes an egress port.

Figure 9:
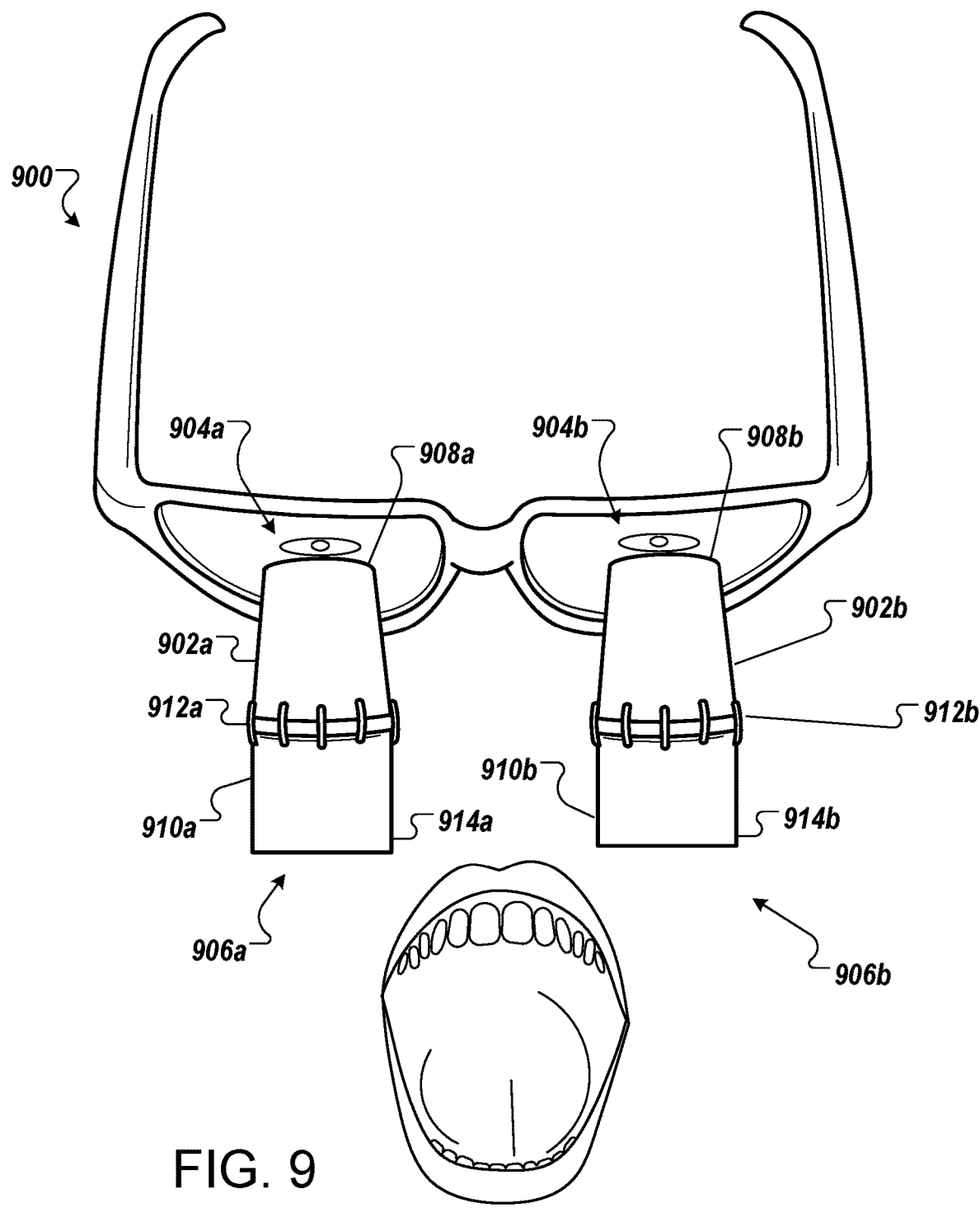
FIG. 9 shows a top view of a coupleable-housed device.

FIG. 9 shows a top view of a coupleable-housed device 900. FIG. 10 shows a side view of the coupleable-housed device 900. FIG. 11 shows a side view of the coupleable-housed device 900. In general, where the device 500 included a single integral housing to hold the redirection member 510 and the magnification member, the device 900 has an integral housing to hold the magnification member while a coupleable housing 914 holds a redirection member 910. This can allow for, for example, the redirection member 910 to be attached to and removed from loupes 902.

Device 900 includes two loupes 902 that each has a coupling fixture 912 used to couple a coupleable housing 914 distinct from the integral housing of the loupe. The coupleable housing 914 can fixedly secure the redirection member 910.

The coupleable housing 914 of each loupe 902 can be removably coupled to the integral housing of the loupe. For example, the wearer may attach and remove the coupleable housing 914. With the coupleable housing 914 removed, the loupes 902 can provide the wearer with a magnified view of the environment from substantially the same point of view as their unmagnified view through the lenses of the PPE glasses. With the coupleable housing 914 removed, the loupes 902 can provide the wearer with a magnified view of an environment from a substantially different point of view of the environment (e.g., offset by 90° or a different angle).

In some implementations, the fixture 912 includes a friction fitting. For example, mating surfaces on the integral housing may mate with mating surfaces of the coupleable housing 914, and surface friction may operate to couple the portions of the loupe 902 together. In some implementations, the fixture 912 includes a snap fitting. For example, tabs in the integral housing may, when pressed on by slots of the coupleable housing 914, momentarily deform and then return to position to lock the portions of the loupe 902 together. In some implementations, the fixture 912 includes a threaded screw. For example, raised threads in the integral housing may interface with recessed threads in the coupleable housing 914 to secure the portions of the loupe 902. In some implementations, the fixture 912 includes an adhesive. For example, a temporary adhesive (e.g., a gum, a cement, glue) may be placed on one or more mating surfaces, including those already discussed here. In some implementations, the fixture 912 includes a weld. For example, a temperature or chemical welding process may be used to permanently mate two mating surfaces, including those already discussed here.

Each loupe 502, 902 includes a proximal end 504, 904 and a distal end 506, 906. When worn by the wearer, the proximal end 504, 904 is near the wearer and the distal end 506, 906 is away from the wearer. As shown, the viewport 508, 908 is fixedly secured at the proximal end 504, 904, and the redirection member 510, 910 is fixedly secured in the distal end 506, 906. Within the integral housing is fixedly secured a magnification member (e.g., lens 219) between the proximal end 504, 904 and the distal end 506, 906.

Each coupleable housing 914 includes an ingress port positioned to deliver ingress light to the redirection member and an egress port is positioned to delivery egress light to a loupe while the coupling housing 914 couples the coupleable optical device to the loupe 902. For example, for a prism may have a first surface into which light is ingressed and a second surface from which light is egressed. The ingress light is angularly offset from the egress light, for example, by the structure of the prism, such that a view axis of the loupe is angularly offset from the ingress light while the optical device is coupled to the loupe.

Figure 12:
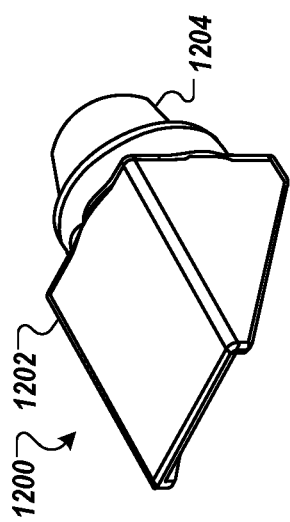
FIG. 12 shows a perspective view of a second coupleable-housed device.
Figure 18:
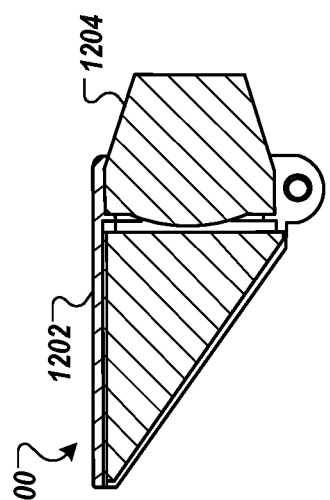
FIG. 18 shows a cut-away side view of the second coupleable-housed device.
Figure 15:
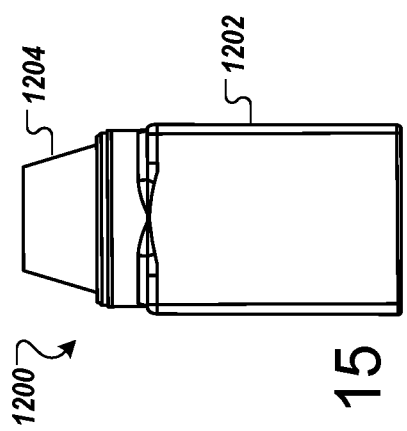
FIG. 15 shows a top view of the second coupleable-housed device.
Figures 14, 17:
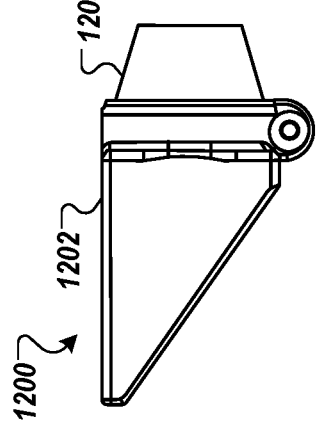
FIGS. 13 and 14 show side views of the second coupleable-housed device.
FIG. 17 shows a front view of the second coupleable-housed device.
Figure 16:
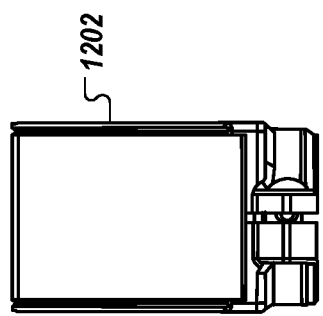
FIG. 16 shows a bottom view of the second coupleable-housed device.
Figure 13:
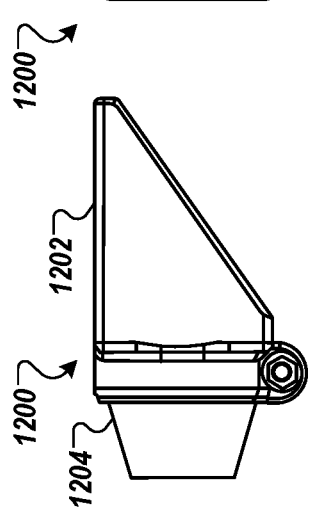

FIG. 12 shows a perspective view of a second coupleable-housed device 1200. FIGS. 13 and 14 show side views of the second coupleable-housed device 1200. FIG. 15 shows a top view of the second coupleable-housed device 1200. FIG. 16 shows a bottom view of the second coupleable-housed device 1200. FIG. 17 shows a front view of the second coupleable-housed device 1200. FIG. 18 shows a cut-away side view of the second coupleable-housed device 1200. The second coupleable-housed device 1200 includes a coupleable housing 1202 and a loupe 1204.

Figure 19:
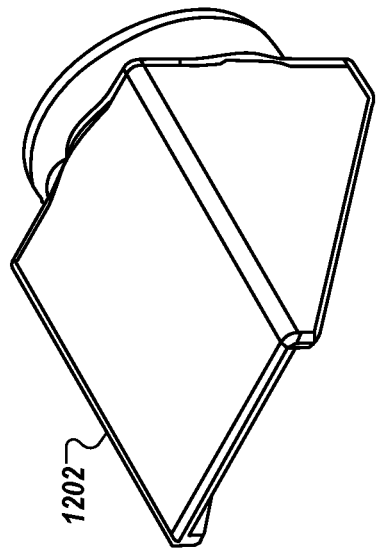
FIG. 19 shows a perspective view of the coupleable housing of the second coupleable-housed device.
Figure 20:
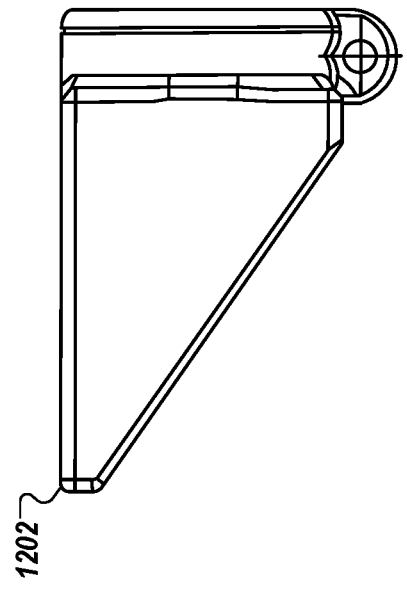
FIG. 20 shows a side view of the coupleable housing of the second coupleable-housed device.
Figure 21:
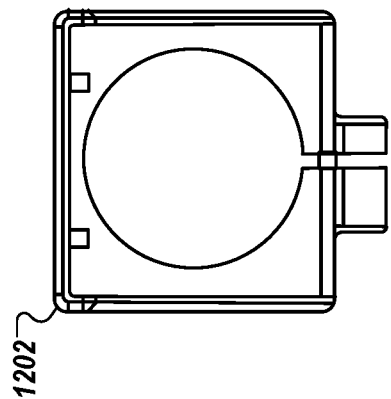
FIG. 21 shows a front view of the coupleable housing of the second coupleable-housed device.

FIG. 19 shows a perspective view of the coupleable housing 1202 of the second coupleable-housed device 1200. FIG. 20 shows a side view of the coupleable housing 1200 of the second coupleable-housed device 1202. FIG. 21 shows a front view of the coupleable housing 1200 of the second coupleable-housed device 1202.

Figure 23:
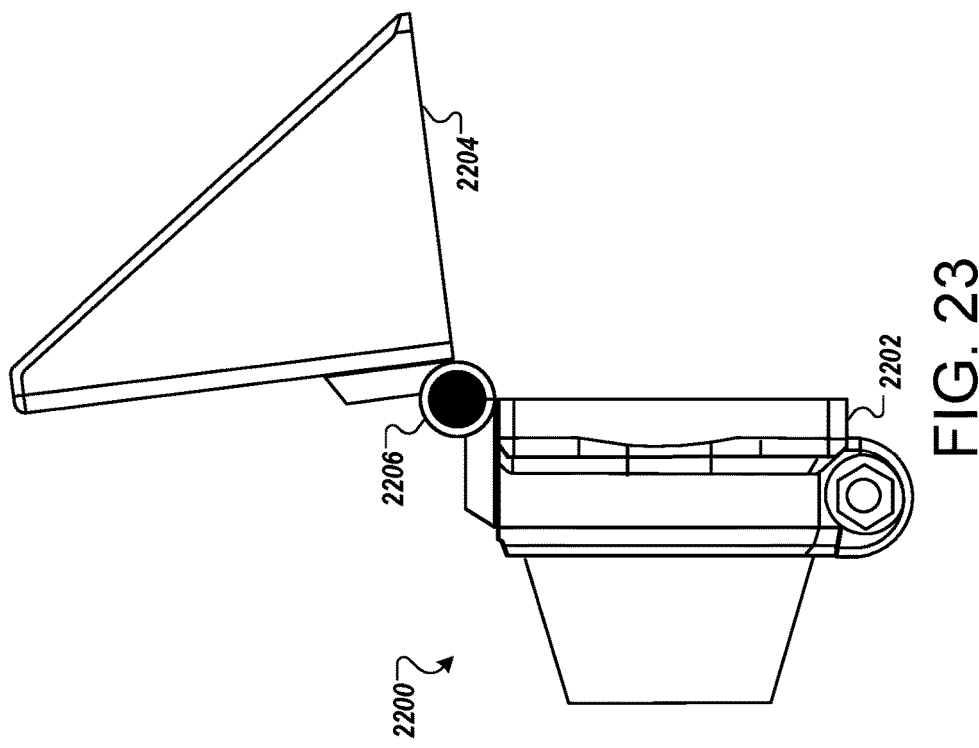
FIGS. 22 and 23 show side views of a coupleable-housing device with a hinged housing Like reference symbols in the various drawings indicate like elements.
Figure 22:
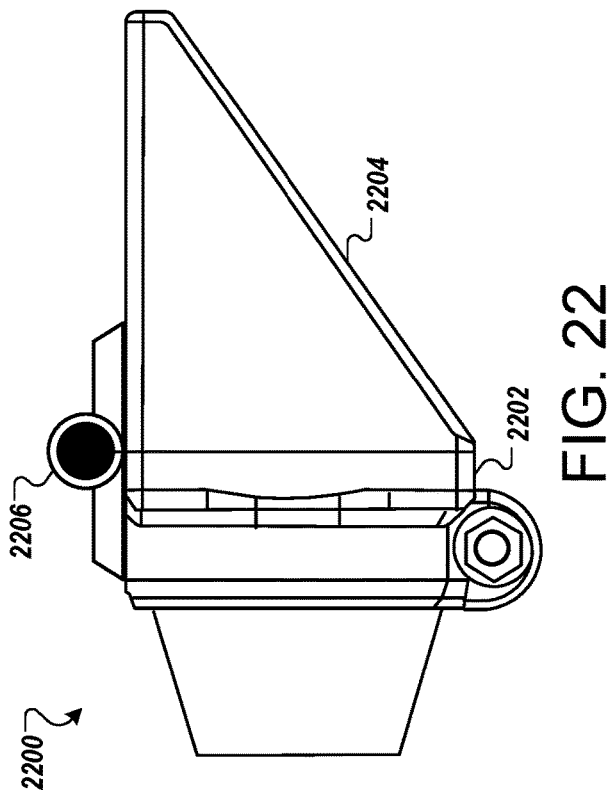

FIGS. 22 and 23 show side views of a coupleable-housing device 2200 with a hinged housing. The device 2200 may allow the user of the device 2200 to engage or disengage the redirection features of the device 2200. That is to say, when the user wants to view what is directly in front of their head, they may flip up a portion of the device 2200, and when the user would like to look down (e.g., at a patient) with a neutral head position, the user may flip that portion down.

The hinged housing of the device 2200 includes a stationary portion 2202 that can removably couple to a magnification loupe. As will be understood, the hinge features may also be used in a fixedly coupled device such as the device 400.

A movable portion 2204 of the hinged housing can rotate about a hinge 2206, which is secured to both the stationary portion 2202 and the movable portion 2204. With the movable portion 2204 elevated (e.g., FIG. 23), the redirection member (e.g., prism) may be moved out of the view path of the user, resulting in an undirected view. With the movable portion 2204 lowered (e.g., FIG. 22), the redirection member (e.g., prism) may be moved into the view path of the user, resulting in a redirected view.

The hinge may be configured to be bias toward two positions that can be called an "open" position and a "closed" position. This bias may be accomplished by with the use of a spring, detent, geometry of the hinge, etc. This can allow the movable member 2204 to be held in place in the open or closed position and prevent unwanted wobble and movement as the user moves their head, speaks, etc. Further, this can allow the user to "snap" or "flick" the movable member 2204 in place with their fingers or head motion.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in appropriate cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the implementations described above should not be understood as requiring such separation in all implementations, and it should be understood that the described components and systems can generally be integrated together in a single product or packaged into multiple products.

Thus, particular implementations of the subject matter have been described. Other implementations are within the scope of the following claims. In some cases, the actions recited in the claims can be performed in a different order and still achieve desirable results.

What is claimed is:
1. A wearable device comprising:
one or more lenses comprising a transparent material;
a first redirection-magnification subassembly and a second redirection-magnification subassembly, each of the redirection-magnification subassemblies being separately secured to the one or more lenses and comprising:
a viewport at a proximal end of the redirection-magnification subassembly shaped to allow projection of an offset and magnified view in a projection direction;
a redirection member;
a magnification member;

an ingress port at a distal end of the redirection-magnification subassembly shaped to allow ingress of light at an offset-angle from the projection direction; and an integral housing that, when assembled, forms a single housing that houses the viewport, the redirection member, the magnification member and the ingress port, including rigidly holding the ingress port at a consistent location and orientation relative to the viewport;

wherein the redirection members comprises an optical prism, the optical prism comprising:
- a first surface into which light ingresses into the optical prism; and
- a second surface from which light egresses from the optical prism; and wherein the first surface is offset from the second surface by the offset-angle.

2. The wearable device of claim 1, wherein the wearable device is a personal protection equipment (PPE) device.

3. The wearable device of claim 1, wherein at least a portion of a proximal end of one of the integral housings passes through at least a portion of the one or more lenses.

4. The wearable device of claim 1, wherein each of the integral housings includes a multi-part clamshell with snap-fasteners.

5. The wearable device of claim 1, wherein each of the integral housings includes one or more indexing surfaces to hold the redirection member and the magnification member.

6. The wearable device of claim 1, wherein each of the integral housings includes at least one metal element secured with at least one removable fastener.

7. The wearable device of claim 6, wherein the removable fastener is one of the group consisting of bolts, pins, and roll-pins.

8. The wearable device of claim 1, wherein each of the integral housings includes an adhesive that secures together two or more elements of the integral housing.

9. The wearable device of claim 8, wherein the adhesive is one of the group consisting of an epoxy and a cyanoacrylate.

10. The wearable device of claim 1, wherein each prism further comprises a third surface and a fourth surface, the third surface being parallel with the fourth surface.

11. The wearable device of claim 1, wherein each prism further comprises another surface that is not parallel to the first surface.

12. The wearable device of claim 1, wherein each prism has a triangular cross-section.

13. The wearable device of claim 1, wherein each prism has a rectangular cross-section.

14. The wearable device of claim 1, wherein lens is one of the group consisting of clear and tinted.

15. The wearable device of claim 1, wherein the one or more lenses comprises a first lens and a second lens, the first redirection-magnification subassembly being secured through the first lens and the second redirection-magnification subassembly being secured through the second lens.

16. The wearable device of claim 1, wherein the one or more lenses are a face shield.

17. The wearable device of claim 1, wherein the wearable device includes contact members having one or more contact-surfaces formed to secure the wearable device to a head of a wearer while the wearer is wearing the device.

18. The wearable device of claim 17, wherein the contact members comprise one or more nose-pads and one or more eye-glass stems.

* * * * *